(12) United States Patent  
Kim et al.

(10) Patent No.: US 9,351,681 B2  
(45) Date of Patent: May 31, 2016

(54) ONE REPETITION MAXIMUM (1RM) ESTIMATING APPARATUS AND METHOD

(71) Applicant: Samsung Electronics Co., Ltd., Suwon-si (KR)

(72) Inventors: Youn Ho Kim, Hwaseong-si (KR); Sang Kon Bae, Seongnam-si (KR); Chang Mok Choi, Seoul (KR); Byung Hoon Ko, Hwaseong-si (KR); Kun Soo Shin, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 84 days.

(21) Appl. No.: 14/083,393

(22) Filed: Nov. 18, 2013

(65) Prior Publication Data

US 2014/0137647 A1    May 22, 2014

(30) Foreign Application Priority Data

Nov. 16, 2012  (KR) .................. 10-2012-0130458

(51) Int. Cl.
```
A63B 24/00      (2006.01)
A61B 5/22       (2006.01)
A61B 5/0488     (2006.01)
A61B 5/00       (2006.01)
```

(52) U.S. Cl.
CPC ............. *A61B 5/224* (2013.01); *A61B 5/0488* (2013.01); *A61B 5/6801* (2013.01); *A61B 5/7235* (2013.01); *A61B 5/7242* (2013.01); *A61B 5/7257* (2013.01)

(58) Field of Classification Search
CPC ....................................................... A63B 24/00

USPC ........................................................ 73/379.01
See application file for complete search history.

(56) References Cited

U.S. PATENT DOCUMENTS

| | | | |
|---|---|---|---|
| 7,753,825 B2 | 7/2010 | Jaquish et al. | |
| 8,217,797 B2 * | 7/2012 | Ikoyan | ...................... 340/573.7 |
| 8,255,079 B2 * | 8/2012 | Linn et al. | ...................... 700/213 |
| 8,562,489 B2 * | 10/2013 | Burton et al. | ...................... 482/9 |
| 8,795,138 B1 * | 8/2014 | Yeh et al. | ........................... 482/8 |
| 9,008,973 B2 * | 4/2015 | French | ............................ 702/19 |
| 2004/0059242 A1 | 3/2004 | Masuo et al. | |
| 2007/0203004 A1 | 8/2007 | Campanaro et al. | |
| 2007/0219051 A1 | 9/2007 | Hayashino et al. | |
| 2008/0204225 A1 | 8/2008 | Kitchen | |

(Continued)

FOREIGN PATENT DOCUMENTS

| | | |
|---|---|---|
| CN | 101513567 A | 8/2009 |
| CN | 102646149 A | 8/2012 |

(Continued)

OTHER PUBLICATIONS

A. de Souza et al. "Lumbar muscles recruitment during resistance exercise for upper limbs," *Journal of Electromyography and Kinesiology*, vol. 19, No. 5, Oct. 1, 2009, pp. 737-745.

(Continued)

*Primary Examiner* — Lisa Caputo  
*Assistant Examiner* — Jamel Williams  
(74) *Attorney, Agent, or Firm* — NSIP Law

(57) ABSTRACT

A one repetition maximum (1RM) estimating apparatus includes a potential signal receiving unit configured to receive a potential signal of a muscle from a sensor attached to a user, and a 1RM estimating unit configured to estimate a 1RM of the user based on the potential signal.

15 Claims, 12 Drawing Sheets

(56) References Cited

U.S. PATENT DOCUMENTS

2009/0181834 A1 7/2009 Campanaro et al.
2009/0286657 A1 11/2009 Sveshnikov

FOREIGN PATENT DOCUMENTS

| | | | |
|---|---|---|---|
| CN | 202654138 | U | 1/2013 |
| CN | 104768462 | A | 7/2015 |
| EP | 1 413 250 | A1 | 4/2004 |
| EP | 2732763 | A1 * | 5/2014 |
| JP | 2008-237798 | A | 10/2008 |
| JP | 2011-45566 | A | 3/2011 |
| KR | 10-0408698 | B1 | 12/2003 |
| KR | 10-0690331 | B1 | 3/2007 |
| KR | 10-2011-0022548 | A | 3/2011 |
| KR | 10-2011-0023815 | A | 3/2011 |
| KR | 10-2012-0067986 | A | 6/2012 |
| WO | WO 2007/021062 | A1 | 2/2007 |
| WO | WO 2007021062 | A1 * | 2/2007 |

OTHER PUBLICATIONS

Extended European Search Report issued Feb. 26, 2014 in counterpart European Patent Application No. 13192609.9. (7 pages in English).

Mobasser, F. et al., "Estimation of elbow-induced wrist force with EMG signals using fast orthogonal search," IEEE Transactions on Biomedical Engineering, vol. 54.4, Apr. 2007 (pp. 683-693).

Chinese Office Action issued on Feb. 25, 2016 in counterpart Chinese Application No. 201310495235.8 (8 pages in English; 7 pages in Chinese).

* cited by examiner

FIG. 10
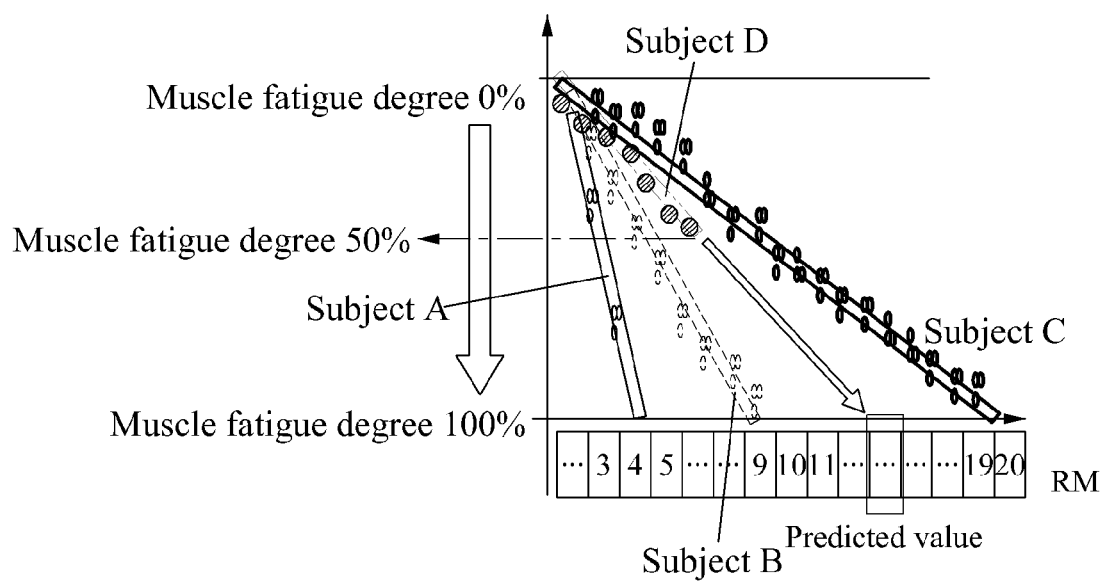
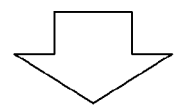
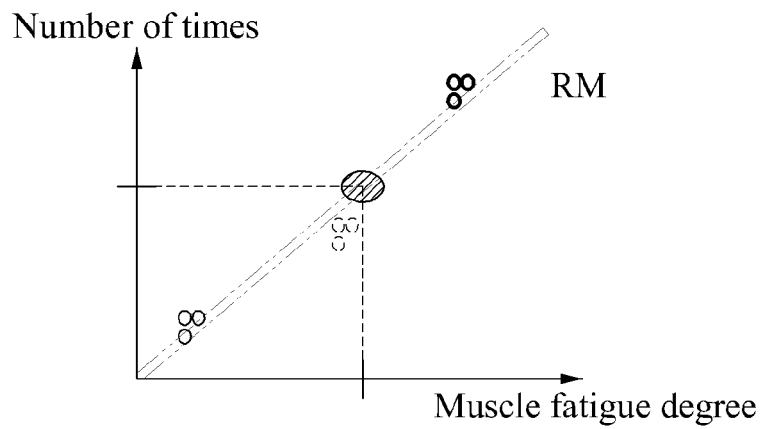

ONE REPETITION MAXIMUM (1RM) ESTIMATING APPARATUS AND METHOD

CROSS-REFERENCE TO RELATED APPLICATIONS

This application claims the benefit under 35 USC 119(a) of Korean Patent Application No. 10-2012-0130458 filed on Nov. 16, 2012, in the Korean Intellectual Property Office, the disclosure of which is incorporated herein by reference in its entirety for all purposes.

BACKGROUND

1. Field

The following description relates to an apparatus and method for estimating a one repetition maximum (1RM) of a user using a sensor.

2. Description of Related Art

In a conventional method of measuring a one repetition maximum (1RM) of a user, the user lifts a suitable amount of a weight until a maximum muscular strength of the user is exhausted. The 1RM of the user may be measured by using a look-up table. In addition, the 1RM of the user may be measured using a separate muscle mass measuring apparatus. The 1RM of the user may be measured with respect to 100% of a muscular strength of the user.

However, measuring the 1RM of the user using such a measuring conventional method may be difficult because the conventional measuring method may injure a user's body because the user may be requested to lift a weight repeatedly until the maximum muscular strength is exhausted. Accordingly, the user's body may be injured, resulting in a muscular pain or injury. In addition, the user may expend a considerable amount of time until the measurement is completed.

SUMMARY

In one general aspect, an apparatus for estimating a one repetition maximum (1RM) includes a potential signal receiving unit configured to receive a potential signal of a muscle from a sensor attached to a user; and a 1RM estimating unit configured to estimate a 1RM of the user based on the potential signal.

The 1RM estimating unit may include an envelope determining unit configured to determine an envelope of amplitudes of the potential signal; a frequency spectrum determining unit configured to determine a mean frequency of a frequency spectrum of the potential signal; and a gradient determining unit configured to determine a gradient based on the envelope and the mean frequency of the frequency spectrum.

The envelope determining unit may be further configured to determine the envelope based on an absolute value of the potential signal.

The frequency spectrum determining unit may be further configured to determine the mean frequency of the frequency spectrum based on the potential signal sampled at predetermined intervals based on a maximum value of the envelope.

The gradient determining unit may be further configured to determine the gradient based on a plurality of feature points in the mean frequency of the frequency spectrum corresponding to peaks of the envelope.

In another general aspect, an apparatus for estimating a one repetition maximum (1RM) includes a sensing unit configured to sense a potential signal of a muscle of a user; and a 1RM estimating unit configured to estimate a 1RM of the user based on the potential signal.

The 1RM estimating unit may include an envelope determining unit configured to determine an envelope of amplitudes of the potential signal; a frequency spectrum determining unit configured to determine a mean frequency of a frequency spectrum of the potential signal; and a gradient determining unit configured to determine a gradient based on the envelope and the mean frequency of the frequency spectrum.

The envelope determining unit may be further configured to determine the envelope based on an absolute value of the potential signal.

The frequency spectrum determining unit may be further configured to determine the mean frequency of the frequency spectrum based on the potential signal sampled at predetermined intervals based on a maximum value of the envelope.

The gradient determining unit may be further configured to determine the gradient based on a plurality of feature points in the mean frequency of the frequency spectrum corresponding to peaks of the envelope.

In another general aspect, a method of estimating a one repetition maximum (1RM) includes receiving a potential signal of a muscle from a sensor attached to a user; and estimating a 1RM of the user based on the potential signal.

The estimating may include determining an envelope of amplitudes of the potential signal; determining a mean frequency of a frequency spectrum of the potential signal; and determining a gradient based on the envelope and the mean frequency of the frequency spectrum.

The determining of the envelope may include determining the envelope based on an absolute value of the potential signal.

The determining of the mean frequency of the frequency spectrum may include determining the mean frequency of the frequency spectrum based on the potential signal sampled at predetermined intervals based on a maximum value of the envelope.

The determining of the gradient may include determining the gradient based on a plurality of feature points in the mean frequency of the frequency spectrum corresponding to peaks of the envelope.

In another general aspect, a method of estimating a one repetition maximum (1RM) includes sensing a potential signal of a muscle of a user; and estimating a 1RM of the user based on the potential signal.

The estimating may include determining an envelope of amplitudes of the potential signal; determining a mean frequency of a frequency spectrum of the potential signal; and determining a gradient based on the envelope and the mean frequency of the frequency spectrum.

The determining of the envelope may include determining the envelope based on an absolute value of the potential signal.

The determining of the mean frequency of the frequency spectrum may include determining the mean frequency of the frequency spectrum based on the potential signal sampled at predetermined intervals based on a maximum value of the envelope.

The determining of the gradient may include determining the gradient based on a plurality of feature points in the mean frequency of the frequency spectrum corresponding to peaks of the envelope.

BRIEF DESCRIPTION OF THE DRAWINGS

FIG. 10 is a graph illustrating an example of a change in a normalized mean frequency of a frequency spectrum of a potential signal of a muscle based on a muscle fatigue degree of a user.

DETAILED DESCRIPTION

Figure 1:
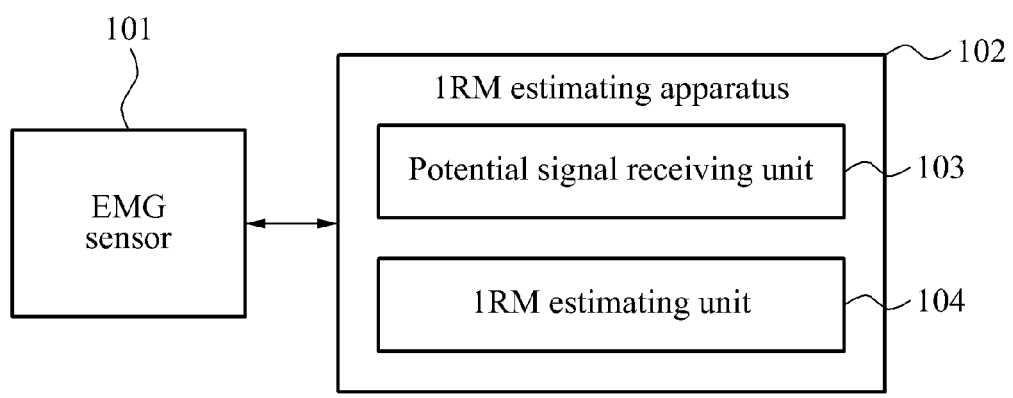
FIG. 1 is a block diagram illustrating an example of a one repetition maximum (1RM) estimating apparatus.

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, description of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

FIG. 1 is a block diagram illustrating an example of a one repetition maximum (1RM) estimating apparatus 102. Referring to FIG. 1, the 1RM estimating apparatus 102 includes a potential signal receiving unit 103 and a 1RM estimating unit 104. The 1RM estimating apparatus 102 may be separated from an electromyography (EMG) sensor 101, and may be included in a user terminal capable of communicating with the EMG sensor 101 wirelessly.

The EMG sensor 101 may be attached to a skin of a user. The EMG sensor 101 may measure a potential signal of a muscle of the user. To measure the potential signal of the muscle, the user may repeatedly lift a weight less than a maximum weight that the user can lift. As an example, the user may repeatedly lift a weight of 20 kilograms (kg) that is 50% of a maximum weight of 40 kg that the user can lift. Accordingly, fatigue and an amount of time to be expended for measuring the potential signal of the muscle may be minimized since the user repeatedly lifts the weight less than the maximum weight that the user can lift.

The EMG sensor 101 may determine an intensity of the measured potential signal of the muscle. The EMG sensor 101 may amplify the potential signal of the muscle based on the intensity of the potential signal. As an example, when the intensity of the potential signal of the muscle is relatively weak, the EMG sensor 101 may amplify the potential signal of the muscle to obtain a signal large enough to be analyzed. In addition, the EMG sensor 101 may transmit the potential signal of the muscle to the 1RM estimating apparatus 102.

The potential signal receiving unit 103 may receive the potential signal of the muscle from the EMG sensor 101.

The 1RM estimating unit 104 may estimate a 1RM of the user based on the received potential signal of the muscle. The 1RM estimating unit 104 may determine an envelope of amplitudes of the potential signal, may determine a mean frequency of a frequency spectrum of the potential signal, and may determine a gradient based on the envelope of the amplitudes of the potential signal and the mean frequency of the frequency spectrum.

The 1RM estimating unit 104 may estimate the 1RM of the user based on the determined gradient. The 1RM estimating apparatus 102 may display the envelope of the amplitudes of the potential signal and the mean frequency of the frequency spectrum to the user.

The 1RM estimating apparatus 102 may provide an exercise program suitable for an exercise ability of the used based on the 1RM of the user.

The 1RM estimating apparatus 102 may estimate the 1RM of the user using a weight less than a maximum weight that the user can lift, thereby stably and rapidly estimating a 1RM using a relatively small amount of time and power of the user. In addition, the 1RM estimating apparatus 102 may evaluate a maximum muscular strength of the user using a reasonable weight, and may determine an objective and quantitative exercise load of the user.

Figure 2:
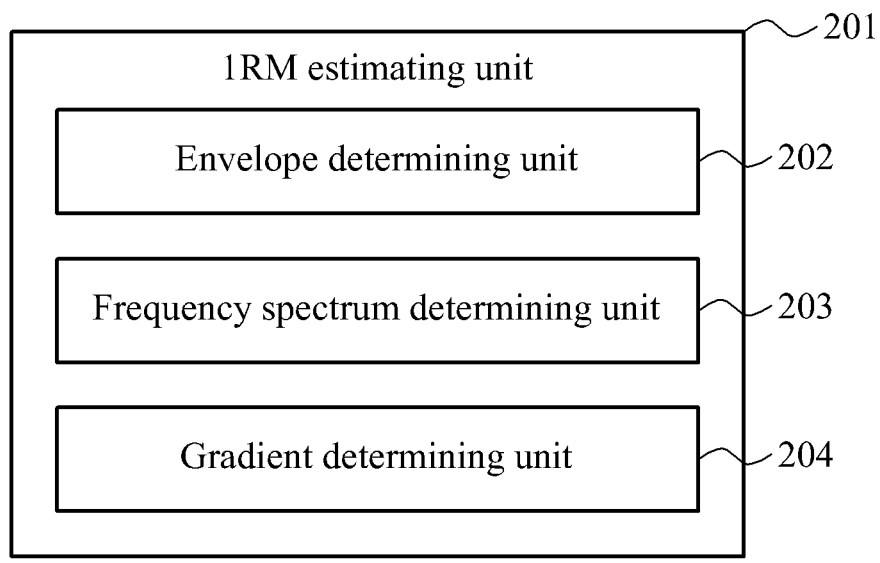
FIG. 2 is a block diagram illustrating an example of a 1RM estimating unit included in a 1RM estimating apparatus.

FIG. 2 is a block diagram illustrating an example of a 1RM estimating unit 201 included in a 1RM estimating apparatus. Referring to FIG. 2, the 1RM estimating unit 201 includes an envelope determining unit 202, a frequency spectrum determining unit 203, and a gradient determining unit 204.

The envelope determining unit 202 may determine an envelope of amplitudes of a potential signal. The envelope determining unit 202 may determine the envelope based on an absolute value of the potential signal. For example, the envelope determining unit 202 may determine the envelope by integrating the absolute value of the potential signal. The envelope determining unit 202 may employ a method of deriving feature points of the potential signal.

The frequency spectrum determining unit 203 may determine a mean frequency of a frequency spectrum of the potential signal. The frequency spectrum determining unit 203 may determine the mean frequency of the frequency spectrum based on a maximum value of the envelope. The frequency spectrum determining unit 203 may use the potential signal sampled at predetermined intervals based on the maximum value of the envelope. The frequency spectrum determining unit 203 may perform frequency conversion of the potential signal sampled at the predetermined intervals. The frequency spectrum determining unit 203 may determine the frequency spectrum by the frequency conversion of the potential signal.

To reduce an amount of calculation required for the frequency conversion, the frequency spectrum determining unit 203 may perform the frequency conversion of the potential signal sampled at the predetermined intervals based on the maximum value of the envelope.

The gradient determining unit 204 may determine a gradient based on the envelope and the mean frequency of the frequency spectrum. The gradient determining unit 204 may determine the gradient based on a plurality of feature points in the mean frequency of the frequency spectrum corresponding to peaks of the envelope. The gradient determining unit 204 may normalize the plurality of feature points. For example, the gradient determining unit 204 may separately normalize feature points differing from each other based on the maximum value among a plurality of feature points input sequentially.

The gradient determining unit 204 may calculate the gradient based on the plurality of normalized feature points. In addition, the gradient determining unit 204 may estimate a 1RM of a user based on the calculated gradient. The gradient calculation will be described in detail below with reference to FIG. 8.

The 1RM estimating apparatus may be configured separately from an EMG sensor. The 1RM estimating apparatus may receive a potential signal of a muscle of a user from the EMG sensor through a wired or wireless communication. The 1RM estimating apparatus configured separately from the EMG sensor may be used in various spaces and places when the user exercises outdoors.

Figure 3:
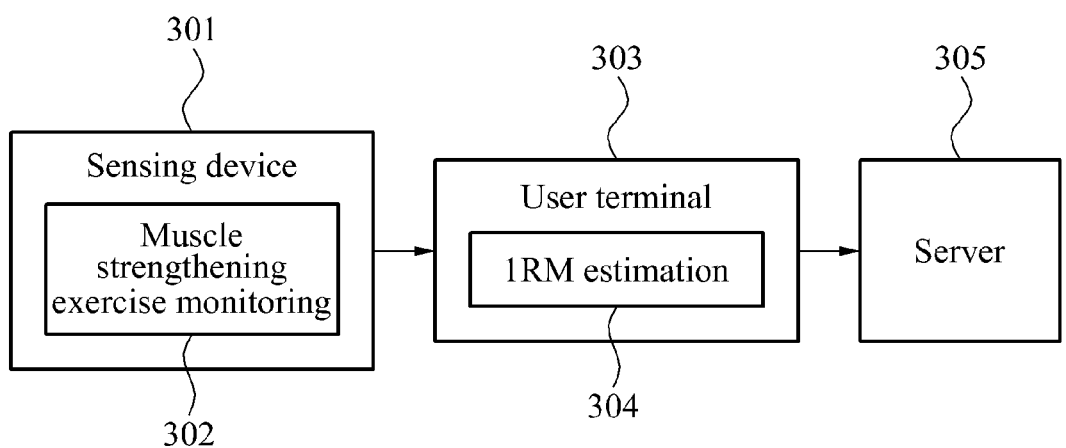
FIG. 3 is a block diagram illustrating an example of an operation of a 1RM estimating apparatus.

FIG. 3 is a block diagram illustrating an example of an operation of a 1RM estimating apparatus. Referring to FIG. 3, a sensing device 301, a user terminal 303, and a server 305 may interoperate with one another. The server 305 may be included or excluded depending on a usage environment of the 1RM estimating apparatus.

The sensing device 301 may be the EMG sensor 101 of FIG. 1. For example, the sensing device 301 may perform muscle strengthening exercise monitoring 302. The sensing device 301 may measure a potential signal of a muscle of a user. The sensing device 301 may differentially amplify the measured potential signal of the muscle based on an intensity. For example, when an intensity of the measured potential signal of the muscle is large enough to be analyzed, the sensing device 301 may not amplify the measured potential signal of the muscle.

The sensing device 301 may be connected to the user terminal 303 and may interoperate with the user terminal 303 using a wireless communication. The sensing device 301 may transmit the measured potential signal of the muscle to the user terminal 303 capable of interoperating with the sensing device 301.

The user terminal 303 may include the 1RM estimating apparatus 102 of FIG. 1. For example, the user terminal 303 may include the 1RM estimating apparatus 102, and may estimate a 1RM of the user. The user terminal 303 may receive the potential signal of the muscle from the sensing device 301. The user terminal 303 may perform 1RM estimation 304. The user terminal 303 may integrate an absolute value of potential signal of a muscle. The user terminal 303 may determine an envelope of amplitudes of the potential signal of the muscle based on the integrated absolute value. In addition, the user terminal 303 may perform frequency conversion of the potential signal sampled at predetermined intervals based on a maximum value of the envelope using a mean frequency.

The user terminal 303 may extract a plurality of feature points in the mean frequency of the frequency spectrum corresponding to peaks of the envelope. The user terminal 303 may normalize the plurality of feature points. The user terminal 303 may estimate the 1RM of the user by calculating a gradient of the plurality of the normalized feature points.

The user terminal 303 may set an exercise goal of the user based on the 1RM of the user. The user terminal 303 may provide the user with the set exercise goal of the user using a speaker or a display.

The server 305 may receive and store the 1RM of the user, and/or the exercise goal of the user set based on the 1RM of the user. The server 305 may share the stored exercise goal of the user through a social network. The server 305 may be included or excluded depending on a usage environment of the 1RM estimating apparatus.

Figure 4:
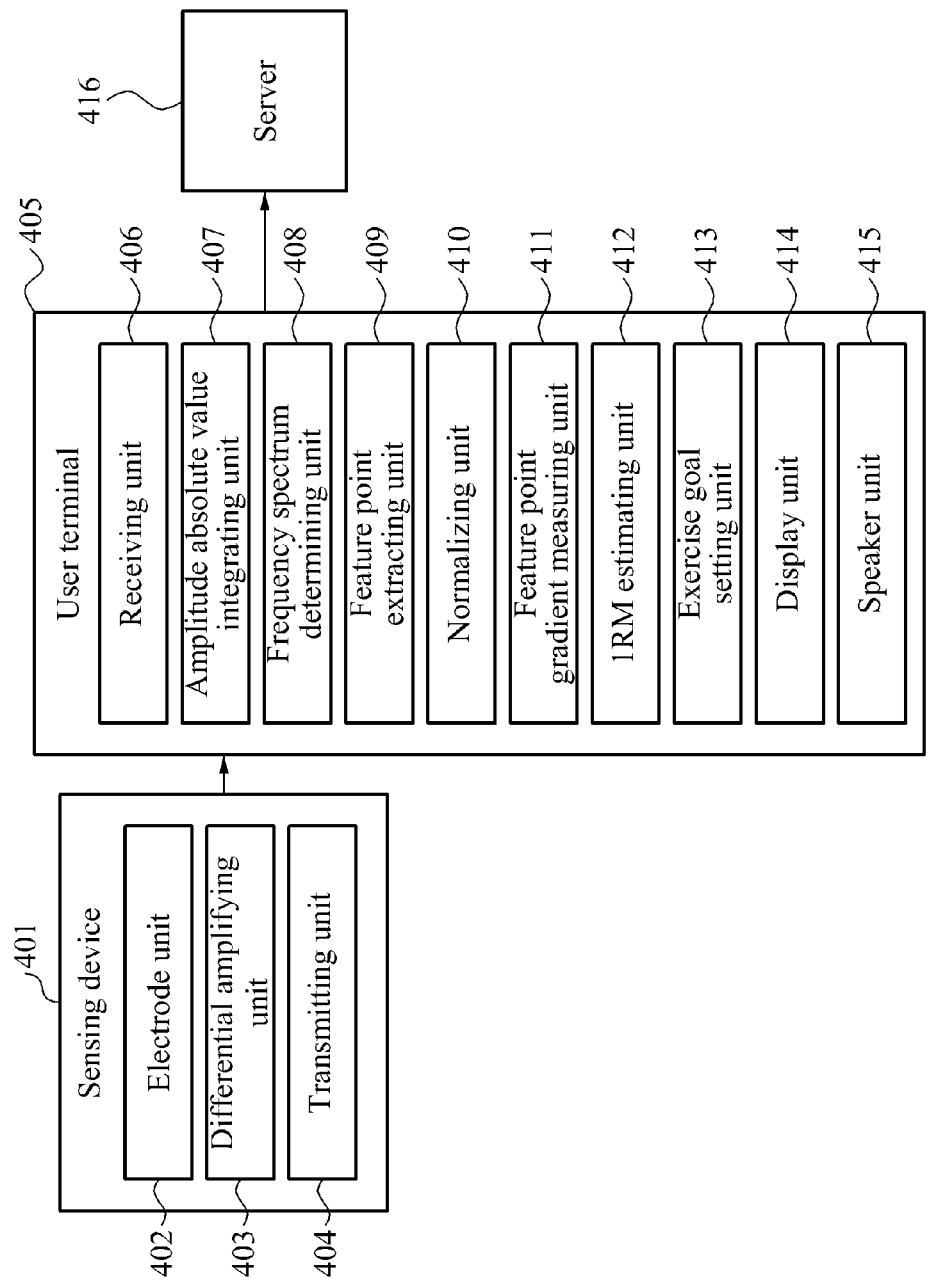
FIG. 4 is a block diagram illustrating an example of a detailed configuration of the 1RM estimating apparatus of FIG. 3.

FIG. 4 is a block diagram illustrating an example of a detailed configuration of the 1RM estimating apparatus of FIG. 3. Referring to FIG. 4, a sensing device 401 includes an electrode unit 402, a differential amplifying unit 403, and a transmitting unit 404. The sensing device 401 may be the EMG sensor 101 of FIG. 1.

The electrode unit 402 may measures a potential signal of a muscle of a user.

The differential amplifying unit 403 differentially amplifies the potential signal based on an intensity of the measured potential signal of the muscle.

The transmitting unit 404 may transmit the amplified potential signal of the muscle to a user terminal capable of receiving the potential signal. The user terminal may be a portable terminal of the user.

A user terminal 405 includes a receiving unit 406, an amplitude absolute value integrating unit 407, a frequency spectrum determining unit 408, a feature point extracting unit 409, a normalizing unit 410, a feature point gradient measuring unit 411, a 1RM estimating unit 412, an exercise goal setting unit 413, and a display unit 414. Depending on a usage environment, the user terminal 405 may further include a speaker unit 415.

The receiving unit 406 may receive a potential signal from the transmitting unit 404 of the sensing device 401. The potential signal may be an amplified potential signal amplified based on an intensity of the measured potential signal. The receiving unit 406 may receive the potential signal in real time.

The amplitude absolute value integrating unit 407 integrates an absolute value of the received potential signal of the muscle. For example, the amplitude absolute value integrating unit 407 may obtain an absolute value of the potential signal of the muscle. The amplitude absolute value integrating unit 407 may integrate the absolute value of the potential signal of the muscle. The amplitude absolute value integrating unit 407 may determine an envelope of amplitudes of the potential signal of the muscle based on the integrated absolute value.

The frequency spectrum determining unit 408 may determine a mean frequency of a frequency spectrum of the potential signal of the muscle. For example, the frequency spectrum determining unit 408 may perform frequency conversion of the potential signal sampled at predetermined intervals based on a maximum value of the envelope. The frequency spectrum determining unit 408 may determine the frequency-converted potential signal to be the frequency spectrum. The frequency spectrum determining unit 408 may perform the frequency conversion of the potential signal sampled at the predetermined intervals to minimize an amount of calculation required.

The feature point extracting unit 409 may extract a plurality of feature points in the mean frequency of the frequency spectrum corresponding to peaks of the envelope. The feature point extracting unit 409 may extract the plurality of feature points to measure a muscle fatigue degree of the user from the mean frequency of the frequency spectrum. For example, the feature point extracting unit 409 may extract the plurality of feature points based on the envelope determined by the amplitude absolute value integrating unit 407 and the mean frequency of the frequency spectrum determined by the frequency spectrum determining unit 408.

The normalizing unit 410 normalizes the plurality of extracted feature points. The normalizing unit 410 may normalize feature points differing from each other based on a feature point having a maximum value among the plurality of feature points. The normalizing unit 410 may extract the muscle fatigue degree of the user by normalizing the feature points.

The feature point gradient measuring unit 411 may measure a gradient of the normalized feature points. The feature point gradient measuring unit 411 may calculate a gradient based on a feature point following the feature point having the maximum value among the normalized feature points. The gradient may represent a correlation between the muscle fatigue degree and a number of repetitions of a test for the user. The muscle fatigue degree may increase by a similar level corresponding to an increase in the number of the repetitions of the test for the user. For example, the correlation between the muscle fatigue degree and the number of the repetitions of the test may be a criterion for measuring a 1RM of the user.

For example, the feature point gradient measuring unit 411 may perform a test using 50% of a muscular strength of the user. The feature point gradient measuring unit 411 may verify a state of a muscle fatigue degree for the 50% of the muscular strength of the user. The feature point gradient measuring unit 411 may estimate a state of a muscle fatigue degree for 100% of the muscular strength of the user based on a gradient of the verified muscle fatigue degree. For example, the feature point gradient measuring unit 411 may estimate a maximum number of repetitions of the test in the state of the muscle fatigue degree for the 100% of the muscular strength of the user based on the gradient of the muscle fatigue degree.

For example, the feature point gradient measuring unit 411 may determine an envelope of amplitudes of the potential signal based on the measured potential signal. The feature point gradient measuring unit 411 may determine a mean frequency of a frequency spectrum based on a maximum value of the envelope. The 1RM estimating apparatus divide values of the mean frequency of the frequency spectrum by a maximum value of the mean frequency of the frequency spectrum to perform normalization. By performing the normalization, the feature point gradient measuring unit 411 may calculate a gradient indicating that a value of a feature point decreases as a number of repetitions of a test increases.

The 1RM estimating unit 412 may estimate a 1RM of the user based on the gradient calculated through the test. The 1RM estimating unit 412 may measure the 1RM of the user in view of the number of the repetitions of the test for the feature point based on the calculated gradient and the maximum value.

For example, the 1RM estimating unit 412 may estimate an actually non-measured maximum number of repetitions of the test in a state of 100% of the muscle fatigue degree of the user based on a gradient of a muscle fatigue degree corresponding to the state of 50% of the muscle fatigue degree of the user. The 1RM estimating unit 412 may estimate a 1RM of the user based on the gradient of the muscle fatigue degree.

The 1RM estimating apparatus may use a Wathan equation as a 1RM estimating equation as expressed by the following Equation 1:

$$IRM = \frac{load}{0.488 + (0.538 \cdot e^{-0.075 \cdot REPS})} \quad (1)$$

In Equation 1, load denotes a weight lifted by a muscle, for example, a weight of a dumbbell, and REPS denotes a number of repetitions.

The exercise goal setting unit 413 may set an exercise suitable for the user based on the measured 1RM of the user. For example, the exercise goal setting unit 413 may set a weight, a number of times exercising, and other exercise information for the user based on basic information of the user input by the user. The exercise goal setting unit 413 may set an exercise goal suitable for each type of exercise depending on a type of exercise desired by the user. The exercise goal setting unit 413 will be described in detail below with reference to FIG. 12.

The display unit 414 may display the set exercise goal of the user on the user terminal 405. The display unit 414 may display an exercise condition of the user. For example, the display unit 414 may display a current weight, a current number of times exercising of the user, and other exercise information so the user may verify the weight, the number of times exercising, and the other exercise information. For example, the display unit 414 may display a body weight of the user, a 1RM-measured value of the user, a number of times exercising of the user, a goal, and other user and exercise information. The display unit 414 may display various information associated with the user depending on settings set by the user.

The speaker unit 415 may provide the user with items associated with the set exercise goal of the user through a speaker. The speaker unit 415 may provide the user with the weight, the number of times exercising, and the other exercise information set according to the exercising condition of the user. For example, the speaker unit 415 may provide the user with a number of sets of the exercise currently being performed by the user, or a number of repetitions of the exercise, through the speaker.

The user terminal 405 may be connected with the server 416 and may interoperate with the server 416 using a wireless communication. The server 416 may receive the 1RM of the user and/or the exercise goal of the user set based on the 1RM of the user from the user terminal 405. The server 416 may store the 1RM of the user and/or the exercise goal of the user set based on the 1RM of the user. In addition, the server 416 may be included or excluded depending on a usage environment.

Figure 5:
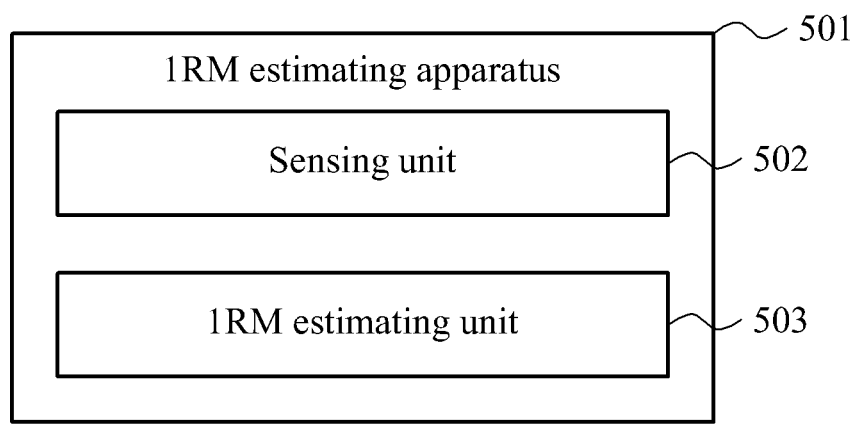
FIG. 5 is a block diagram illustrating another example of a 1RM estimating apparatus.

FIG. 5 is a block diagram illustrating another example of a 1RM estimating apparatus 501. Referring to FIG. 5, the 1RM estimating apparatus 501 includes a sensing unit 502 and a 1RM estimating unit 503. The 1RM estimating apparatus 501 may be included in an EMG sensor to estimate 1RM, and the EMG sensor may transfer the estimated 1RM to a user terminal through a wireless communication.

The sensing unit 502 may sense a potential signal of a muscle from the EMG sensor included in the 1RM estimating apparatus 501. The sensing unit 502 may amplify the potential signal of the muscle to a signal large enough to be analyzed based on an intensity of the potential signal of the muscle.

The IRM estimating unit 503 may estimate a 1RM of the based on the received potential signal of the muscle. The 1RM estimating unit 503 may determine an envelope of amplitudes of the potential signal. The 1RM estimating unit 503 may determine a mean frequency of a frequency spectrum of the potential signal. The 1RM estimating unit 503 may determine a gradient based on the mean frequency of the frequency spectrum and the envelope of the amplitudes of the potential signal. The 1RM estimating unit 503 may estimate the 1RM of the user based on the determined gradient.

The 1RM estimating unit 503 will be described in detail below with reference to FIG. 6.

Figure 6:
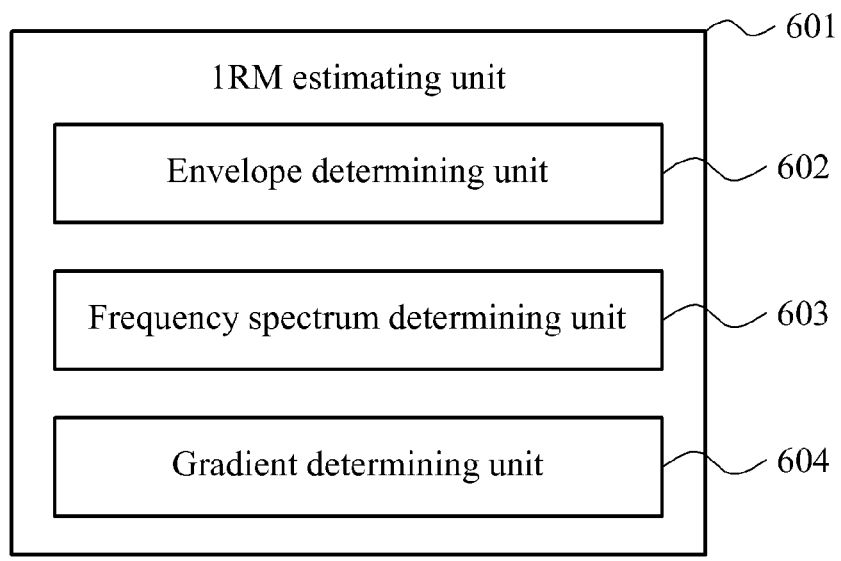
FIG. 6 is a block diagram illustrating another example of a 1RM estimating unit included in a 1RM estimating apparatus.

FIG. 6 is a block diagram illustrating another example of a 1RM estimating unit 601 included in a 1RM estimating apparatus. Referring to FIG. 6, the 1RM estimating unit 601 includes an envelope determining unit 602, a frequency spectrum determining unit 603, and a gradient determining unit 604.

The envelope determining unit 602 may determine an envelope of amplitudes of a potential signal based on an absolute value of the potential signal. For example, the envelope determining unit 602 may determine the envelope by integrating the absolute value of the potential signal.

The frequency spectrum determining unit 603 may determine a mean frequency of a frequency spectrum of a potential signal sampled at predetermined intervals based on a maximum value of the envelope. The frequency spectrum determining unit 603 may determine the frequency spectrum by performing frequency conversion of the potential signal sampled at the predetermined intervals.

The gradient determining unit 604 may determine a gradient based on a plurality of feature points in the mean frequency of the frequency spectrum corresponding to peaks of the envelope. The gradient determining unit 604 may separately normalize feature points differing from each other based on the maximum value among the plurality of feature points input sequentially. In addition, the gradient determining unit 604 may estimate a 1RM of the user based on the gradient calculated based on the plurality of normalized feature points. For example, the gradient determining unit 604 may estimate the 1RM based on a number of feature points according to the gradient.

The 1RM estimating apparatus 601 may be provided in an integrated structure in which an EMG sensor is included. For example, the 1RM estimating apparatus 601 may be included in the EMG sensor.

For example, the 1RM estimating apparatus 601 may include an EMG sensor, and may be attached to a body of the user. The 1RM estimating apparatus 601 may verify a state of a muscle fatigue degree of the user according to a maximum number of repetitions of a test. The 1RM estimating apparatus 601 may measure a maximum number of repetitions of the test corresponding to 50% of a muscular strength of the user. The 1RM estimating apparatus 601 may verify a muscle fatigue degree corresponding to the maximum number of the repetitions of the test. The 1RM estimating apparatus 601 may estimate a muscle fatigue degree of 100% of the muscular strength of the user based on a gradient of the muscle fatigue degree of the user. The 1RM estimating apparatus 601 may estimate a 1RM of the user based on the gradient of the muscle fatigue degree of the user.

Figure 7:
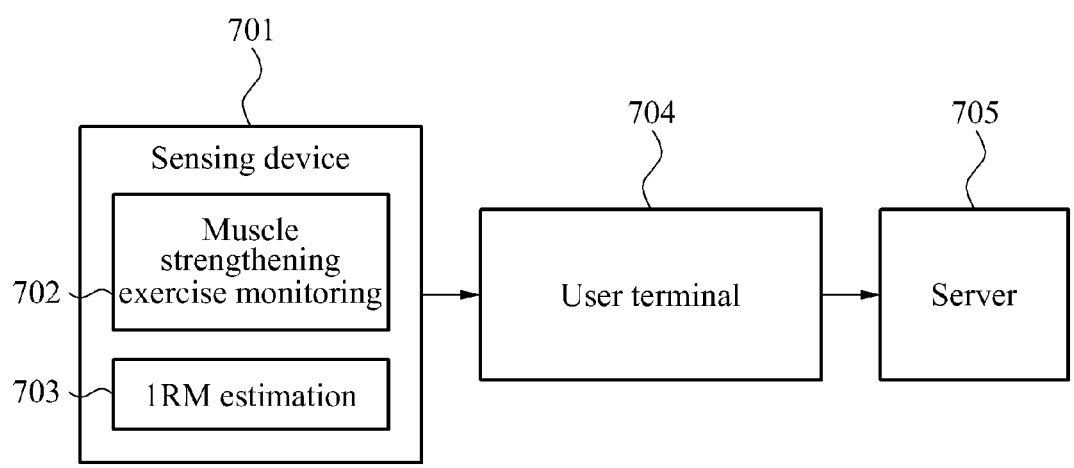
FIG. 7 is a block diagram illustrating another example of an operation of a 1RM estimating apparatus.

FIG. 7 is a block diagram illustrating another example of an operation of a 1RM estimating apparatus. Referring to FIG. 7, a sensing device 701 may perform muscle strengthening exercise monitoring 702, and 1RM estimation 703. The sensing device 701 may be the EMG sensor described with reference to FIG. 5.

The sensing device 701 may include the 1RM estimating apparatus 501 of FIG. 5. For example, the sensing device 701 may estimate a 1RM of a user based on a potential signal of a muscle of the user sensed by the 1RM estimating apparatus.

For example, the sensing device 701 may sense a potential signal of a muscle. The sensing device 701 may differentially amplify the sensed potential signal of the muscle based on an intensity of the potential signal. The sensing device 701 may determine an envelope of amplitudes of the potential signal of the muscle by integrating an absolute value of the potential signal of the muscle. The sensing device 701 may determine a mean frequency of a frequency spectrum by performing frequency conversion of a potential signal sampled at predetermined intervals based on a maximum value of the envelope. The sensing device 701 may estimate a 1RM of the user by extracting a plurality of feature points in the mean frequency of the frequency spectrum corresponding to peaks of the envelope, and multiplexing the plurality of extracted feature points. The sensing device 701 may set an exercise goal suitable for the user based on the 1RM of the user. The sensing device 701 may be connected with a user terminal 704, and may interoperate with the user terminal 704 using a wireless communication.

A server 705 may store the 1RM of the user received from the user terminal 704, and/or the exercise goal of the user set based on the 1RM of the user. The server 705 may interoperate with the user terminal 704 or may not interoperate with the user terminal 705 depending on a usage environment.

Figure 8:
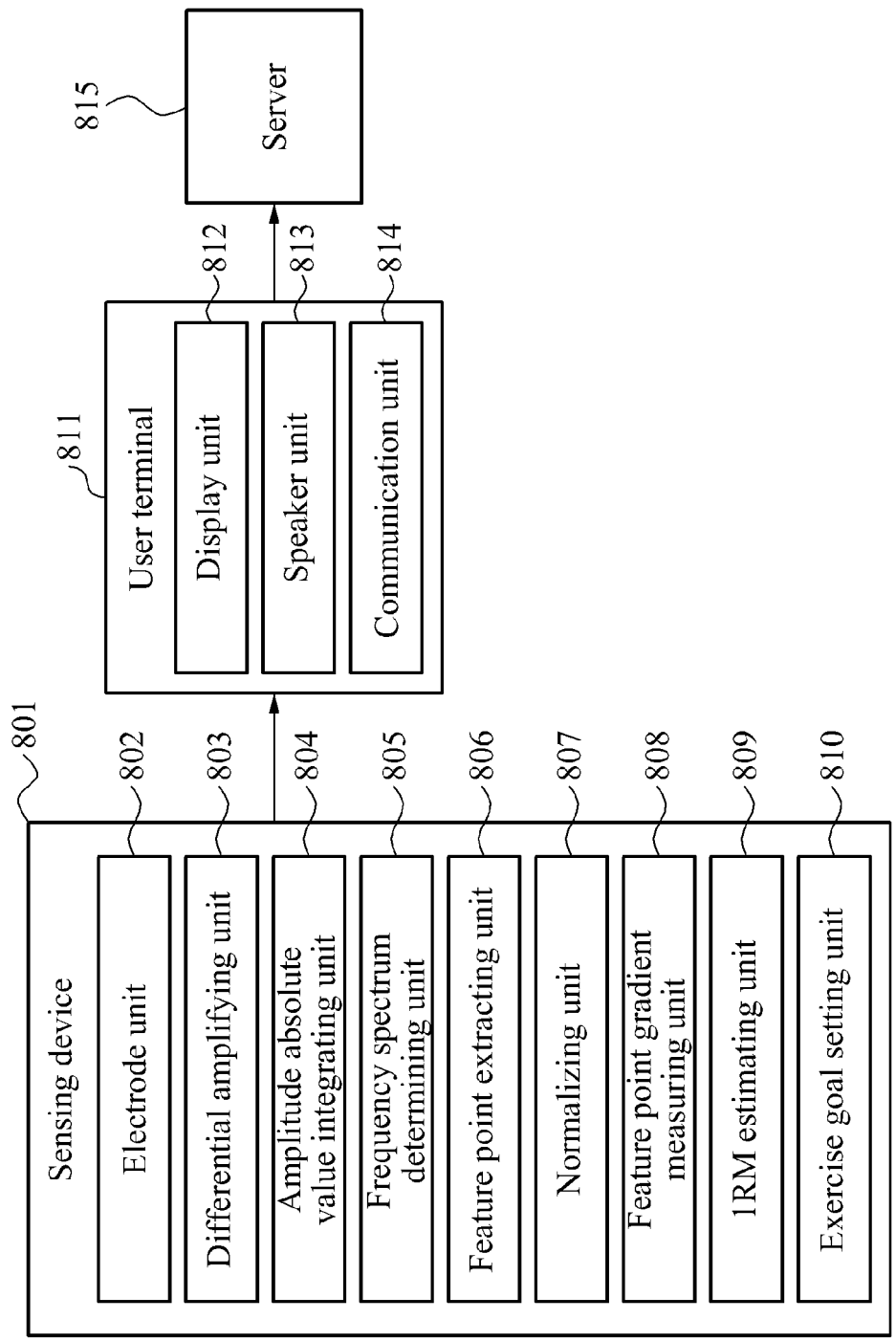
FIG. 8 is a block diagram illustrating an example of a detailed configuration of the 1RM estimating apparatus of FIG. 7.

FIG. 8 is a block diagram illustrating an example of a detailed configuration of the 1RM estimating apparatus of FIG. 7. Referring to FIG. 8, a sensing device 801 includes an electrode unit 802, a differential amplifying unit 803, an amplitude absolute value integrating unit 804, a frequency spectrum determining unit 805, a feature point extracting unit 806, a normalizing unit 807, a feature point gradient measuring unit 808, a 1RM estimating unit 809, and an exercise goal setting unit 810.

The electrode unit 802 may sense a potential signal of a muscle. For example, the electrode unit 802 may sense the potential signal of the muscle of a user. The differential amplifying unit 803 differentially amplifies the sensed potential signal of the muscle based on an intensity of the sensed potential signal.

The amplitude absolute value integrating unit 804 may determine an envelope of amplitudes of the potential signal of the muscle based on an absolute value of the potential signal of the muscle. The amplitude absolute value integrating unit 804 may determine the envelope by integrating the absolute value of the potential signal of the muscle.

The frequency spectrum determining unit 805 may determine a mean frequency of a frequency spectrum by performing frequency conversion of the potential signal sampled at predetermined intervals based on a maximum value of the envelope. The frequency spectrum determining unit 805 may perform the frequency conversion of the potential signal sampled at the predetermined intervals to minimize an amount of calculation required. For example, the frequency conversion may include a fast Fourier transform (FFT) or other frequency conversion known to one of ordinary skill in the art.

The feature point extracting unit 806 extracts a plurality of feature points in the mean frequency of the frequency spectrum corresponding to peaks of the envelope. The feature point extracting unit 806 may extract the plurality of feature points to measure a muscle fatigue degree of the user based on the frequency spectrum.

The normalizing unit 807 normalizes the plurality of extracted feature points. The normalizing unit 807 may normalize feature points differing from each other based on a feature point having a maximum value among the plurality of feature points. The normalizing unit 807 may extract the muscle fatigue degree of the user.

The feature point gradient measuring unit 808 may measure a gradient of a feature point using the plurality of normalized feature points. The feature point gradient measuring unit 808 may calculate a gradient based on the feature point having the maximum value among the normalized feature points.

The 1RM estimating unit 809 may estimate a 1RM of the user based on the calculated gradient. The 1RM estimating unit 809 may measure a number of feature points starting from a feature point having a maximum value of the gradient. The 1RM estimating apparatus 809 may estimate the 1RM of the user based on the measured feature points.

The exercise goal setting unit 810 may set a weight, a number of times exercising, and the other exercise information for the user to be suitable for basic information of the user input by the user based on the measured 1RM of the user. The exercise goal setting unit 810 will be described in detail below with reference to FIG. 12.

A user terminal 811 includes a display unit 812 and a communication unit 814. Depending on a usage environment, the user terminal 811 may further include a speaker unit 813.

The display unit 812 displays the set exercise goal of the user on the user terminal 811. The display unit 812 may display an exercise condition of the user. For example, the display unit 812 may display a current weight, a current number of times exercising of the user, and other exercise information so the user may verify the weight, the number of times exercising, and the other exercise information.

The speaker unit 813 may provide the user with items associated with the set exercise goal of the user through a speaker. The speaker unit 813 may provide the user with the weight, the number of times exercising, and the other exercise information set based on the exercising condition of the user through the speaker.

The communication unit 814 may communicate with the sensing device 801. The communication unit 814 may receive the exercise goal set based on the 1RM of the user and other information.

A server 815 may interoperate with the user terminal 811. The server 815 may receive the 1RM and/or the exercise goal of the user set based on the 1RM from the user terminal 811, and may store the 1RM and/or the exercise goal of the user. In addition, the server 815 may share data regarding the user associated with a social network. The server 815 may interoperate with the user terminal 811 or may not interoperate with the user terminal 811 depending on a usage environment.

The server described with reference to FIGS. 3, 4, 7, and 8 may be included or excluded depending on a usage environment.

Figure 9:
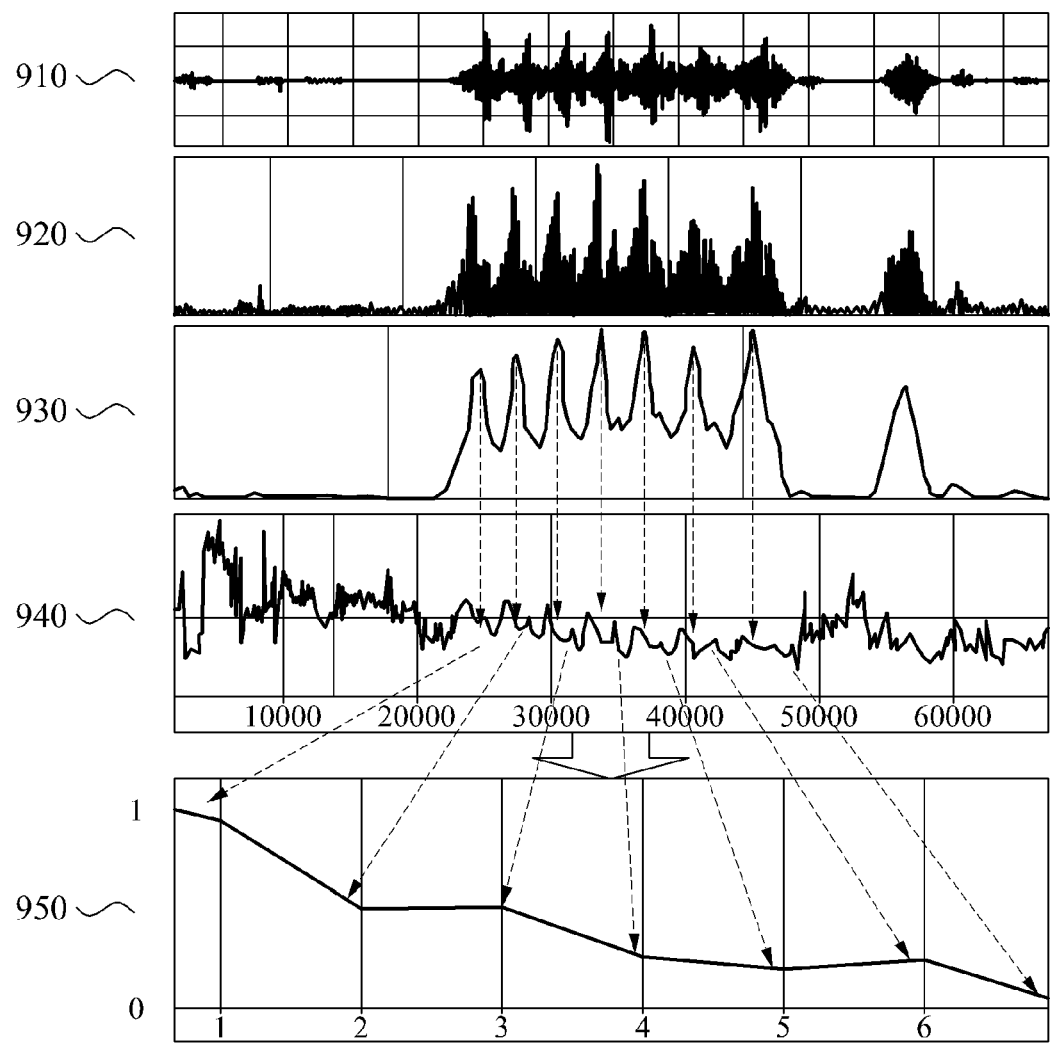
FIG. 9 is a diagram illustrating an example of a process of estimating an actual 1RM.

FIG. 9 is a diagram illustrating an example of a process of estimating an actual 1RM. In operation 910, an EMG sensor or a sensor amplifies a potential signal to obtain a potential signal large enough to be analyzed.

In operation 920, an envelope determining unit may calculate an absolute value of the amplified potential signal relative to an X axis. The envelope determining unit may calculate the absolute value of the potential signal to maximize an intensity of the potential signal.

In operation 930, the envelope determining unit may determine an envelope of amplitudes of the potential signal by integrating the absolute value of the potential signal. The envelope determining unit may extract a maximum value of the envelope to minimize an amount of computation to be performed for extracting feature points.

In operation 940, a frequency spectrum determining unit may determine a mean frequency of a frequency spectrum by performing frequency conversion of the potential signal of operation 910 sampled at predetermined intervals based on the maximum value of the envelope of operation 930. The frequency spectrum determining unit may use the maximum value of the envelope for reducing an amount of computation to be performed to calculate the entire frequency spectrum. The frequency spectrum determining unit may perform frequency conversion of the potential signal sampled at the predetermined intervals based on the maximum value, thereby deriving features of the received or sensed potential signal of the muscle.

In operation 950, a gradient determining unit extracts a plurality of feature points in the mean frequency of the frequency spectrum corresponding to peaks of the envelope of operation 930. The gradient determining unit may normalize the extracted feature points. For example, the gradient determining unit may normalize the extracted feature points based on a feature point having a maximum value among the extracted feature points.

FIG. 10 is a graph illustrating an example of a change in a normalized mean frequency of a frequency spectrum of a potential signal of a muscle based on a muscle fatigue degree of a user. The upper graph in FIG. 10 illustrates 1RMs measured for subjects A, B, C, and D. The subjects A, B, C, and D may be tested using respective predetermined weights. In addition, the subjects A, B, C, and D may perform the test repeatedly until muscle fatigue degrees of the subjects A, B, C, and D reach respective maximum values.

The subjects A, B, and C may perform the test based on a conventional method. For example, the subjects A, B, and C may perform an exercise repeatedly with respective maximum weights that the subjects A, B, and C can lift until muscular strengths of the subjects A, B, and C are exhausted. In the conventional method, a number of repetitions of the test for each subject may be measured. The subjects A, B, and C may have different numbers of repetitions of the test due to different muscular strengths. Based on the numbers of repetitions, different 1RMs may be estimated for the subjects A, B, and C. Referring to the upper graph, the 1RM of the subject C performing the test a greater number of times may be estimated to be higher than the 1RMs of the subjects A and B. However, according to the conventional method, the subjects A, B, and C may be requested to perform the test repeatedly until the respective muscular strengths of the subjects are exhausted to estimate the 1RMs, which may cause bodies of the subjects A, B, and C to be injured.

The subject D may perform the test based on a 1RM estimating method described in this application. As an example, a 1RM of the subject D may be estimated using the 1RM estimating method. The subject D may be tested using a weight less than a maximum weight that the subject D can lift. The subject D may perform an exercise repeatedly until a muscle fatigue degree reaches a maximum value. For example, the subject D may perform the exercise until the muscle fatigue degree reaches the maximum value starting from 0% of the muscle fatigue degree. For example, a number of times exercising at 100% of the muscle fatigue degree may be estimated based on a trend in the muscle fatigue degree until the muscle fatigue degree corresponds to 50%.

In the 1RM estimating method, a maximum number of repetitions of the test may be estimated using a regression equation between a number of times performing a maximum muscular strength exercise and an increase rate of a muscle fatigue degree. In the 1RM estimating method, a characteristic of the muscle fatigue degree increasing as the number of times increases as illustrated in the lower graph in FIG. 10 may be used.

In the 1RM estimating method, the 1RM of the subject D may be estimated by substituting the estimated number of times and a test weight used for estimating 1RM in a 1RM calculating equation. The 1RM calculating equation may be a Wathan equation used for estimating the 1RM, or any one of the other various equations used for estimating the 1RM known to one of ordinary skill in the art.

Figure 11:
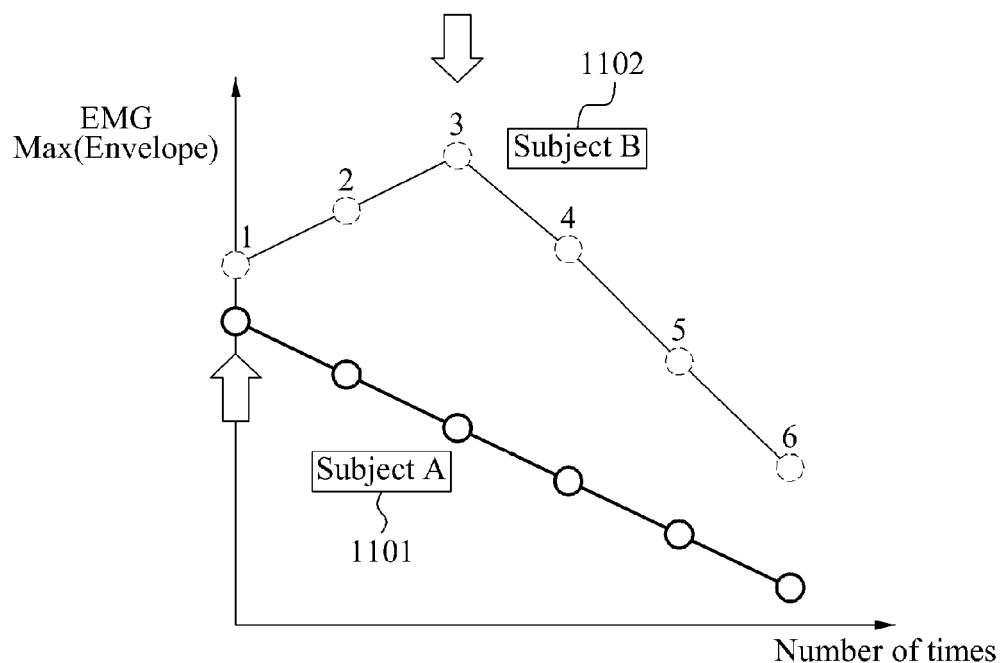
FIG. 11 is a graph illustrating an example of a process of estimating a 1RM using a feature point that is a criterion for a gradient.

FIG. 11 is a graph illustrating an example of a process of estimating 1RM using a feature point that is a criterion for a gradient. Referring to FIG. 11, gradients for a subject A 1101 and a subject B 1102 may be configured in various forms.

A gradient may be measured based on a feature point having a maximum value among a plurality of feature points. The feature points may be feature points in a mean frequency of a frequency spectrum of a potential signal of a muscle corresponding to peaks of an envelope of amplitudes of the potential signal. In a case of the subject A 1101, a gradient determining unit may determine a gradient based on a first feature point having a maximum value among a plurality of feature points. The first feature point may be a reference point in time for estimating a 1RM of a user based on muscular strength exercise. In a case of the subject B 1102, the gradient determining unit may determine a gradient based on a third feature point having a maximum value among a plurality of feature points. The third feature point may be a reference point in time for estimating a 1RM of a user based on muscular strength exercise. The gradient determining unit may calculate a gradient based on feature points following the feature point that is a reference point in time. For example, in the case of the subject A 1101, the gradient determining unit may calculate the gradient based on first to sixth feature points. In the case of the subject B 1102, the gradient determining unit may calculate the gradient based on third to sixth feature points. The gradient determining unit may estimate a 1RM of the user based on the calculated gradient.

A difference between the subject A 1101 and the subject B 1102 may result from a difference in a mean frequency for each user. As the user may perform the 1RM test a greater number of times, a probability that a maximum value of a mean frequency will occur at a first time may decrease. For example, in a case of a user performing the test a relatively greater number of times, a maximum value of a mean frequency may occur after the first to third times from the beginning of the test. Accordingly, the gradient determining unit may calculate the gradient based on a trend line from a position at which the maximum value of the mean frequency for the user occurs to a final time.

The gradient determining unit may obtain the gradient according to the trend line from the number of repetitions of the test until energy of the user performing the test is exhausted based on the maximum value of the mean frequency, thereby estimating the 1RM of the user.

The gradient determining unit of FIG. 8 may be the gradient determining unit 204 of FIG. 2 or the gradient determining unit 604 of FIG. 6.

Figure 12:
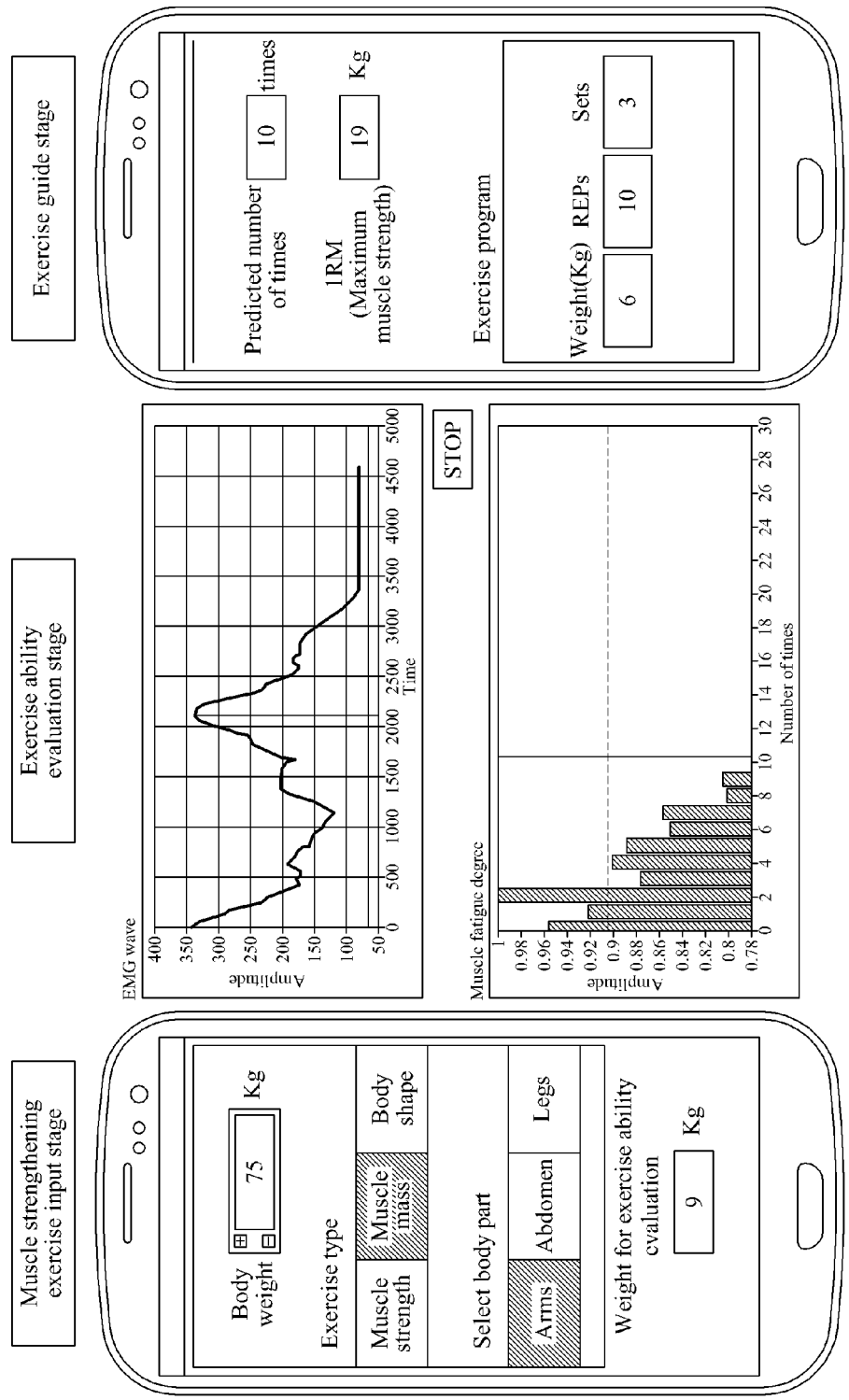
FIG. 12 is a diagram illustrating an example of a process of estimating a 1RM corresponding to an exercise goal of a user and providing an exercise program suitable for the 1RM.

FIG. 12 is a diagram illustrating an example of a process of estimating a 1RM corresponding to an exercise goal of a user and providing an exercise program suitable for the 1RM. Referring to FIG. 12, a 1RM estimating apparatus may receive an input of basic information of a user from the user. For example, the 1RM estimating apparatus may receive an input of information about a body weight of the user, an exercise type, a body part to be exercised, a weight for exercise ability evaluation. The weight for exercise ability evaluation may be used for measuring a 1RM of the user, and may be a weight less than a maximum weight that the user can lift.

The 1RM estimating apparatus may perform exercise ability evaluation of the user based on the basic information of the user. For example, the 1RM estimating apparatus may estimate a 1RM of the user based on a test using the weight for exercise ability evaluation.

The 1RM estimating apparatus may provide an exercise program to the user based on the estimated 1RM and the basic information of the user. For example, the 1RM estimating apparatus may provide a number of repetitions of the test of the user, the 1RM of the user, for example, a maximum muscular strength of the user, and the exercise program based on the test. The exercise program may include exercise information, for example, a weight with which the user may exercise, a number of repetitions of the exercise, a number of sets per time, and other exercise information.

The 1RM estimating apparatus 102, the potential signal receiving unit 103, and the 1RM estimating unit 104 illustrated in FIG. 1, the 1RM estimating unit 201, the envelope determining unit 202, the frequency spectrum determining unit 203, and the gradient determining unit 204 illustrated in FIG. 2, the sensing device 301, the user terminal 303, and the server 305 illustrated in FIG. 3, the sensing device 401, the electrode unit 402, the differential amplifying unit 403, the transmitting unit 404, the user terminal 405, the receiving unit 406, the amplitude absolute value integrating unit 407, the frequency spectrum determining unit 408, the feature point extracting unit 409, the normalizing unit 410, the feature point gradient measuring unit 411, the 1RM estimating unit 412, the exercise goal setting unit 413, the display unit 414, the speaker unit 415, and the server 416 illustrated in FIG. 4, the 1RM estimating apparatus 501, the sensing unit 502, and the 1RM estimating unit 503 illustrated in FIG. 5, the 1RM estimating unit 601, the envelope determining unit 602, the frequency spectrum determining unit 603, and the gradient determining unit 604 illustrated in FIG. 6, the sensing device 701, the user terminal 704, and the server 705 illustrated in FIG. 7, the sensing device 801, the electrode unit 802, the differential amplifying unit 803, the amplitude absolute value integrating unit 804, the frequency spectrum determining unit 805, the feature point extracting unit 806, the normalizing unit 807, the feature point gradient measuring unit 808, the 1RM estimating unit 809, the exercise goal setting unit 810, the user terminal 811, the display unit 812, the speaker unit 813, the communication unit 814, and the server 815 illustrated in FIG. 8, and the 1RM estimating apparatus illustrated in FIG. 12 that perform the operations illustrated in FIGS. 3, 7, and 9-12 may be implemented using one or more hardware components, one or more software components, or a combination of one or more hardware components and one or more software components.

A hardware component may be, for example, a physical device that physically may perform one or more operations, but is not limited thereto. Examples of hardware components include resistors, capacitors, inductors, power supplies, frequency generators, operational amplifiers, power amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An apparatus for estimating a one repetition maximum (1RM), the apparatus comprising:
    a potential signal receiving unit configured to receive a potential signal of a muscle from an electromyography (EMG) sensor attached to a user; and
    a 1RM estimating unit configured to estimate a 1RM of the user based on the potential signal.

2. The apparatus of claim 1, wherein the 1RM estimating unit comprises:
    an envelope determining unit configured to determine an envelope of amplitudes of the potential signal;
    a frequency spectrum determining unit configured to determine a mean frequency of a frequency spectrum of the potential signal; and a gradient determining unit configured to determine a gradient based on the envelope and the mean frequency of the frequency spectrum.

3. The apparatus of claim 2, wherein the envelope determining unit is further configured to determine the envelope based on an absolute value of the potential signal.

4. The apparatus of claim 2, wherein the frequency spectrum determining unit is further configured to determine the mean frequency of the frequency spectrum based on the potential signal sampled at predetermined intervals based on a maximum value of the envelope.

5. The apparatus of claim 2, wherein the gradient determining unit is further configured to determine the gradient based on a plurality of feature points in the mean frequency of the frequency spectrum corresponding to peaks of the envelope.

6. An apparatus for estimating a one repetition maximum (1RM), the apparatus comprising:
 an electromyography (EMG) sensing unit configured to sense a potential signal of a muscle of a user; and
 a 1RM estimating unit configured to estimate a 1RM of the user based on the potential signal.

7. The apparatus of claim 6, wherein the 1RM estimating unit comprises:
 an envelope determining unit configured to determine an envelope of amplitudes of the potential signal;
 a frequency spectrum determining unit configured to determine a mean frequency of a frequency spectrum of the potential signal; and
 a gradient determining unit configured to determine a gradient based on the envelope and the mean frequency of the frequency spectrum.

8. The apparatus of claim 7, wherein the envelope determining unit is further configured to determine the envelope based on an absolute value of the potential signal.

9. The apparatus of claim 7, wherein the frequency spectrum determining unit is further configured to determine the mean frequency of the frequency spectrum based on the potential signal sampled at predetermined intervals based on a maximum value of the envelope.

10. The apparatus of claim 7, wherein the gradient determining unit is further configured to determine the gradient based on a plurality of feature points in the mean frequency of the frequency spectrum corresponding to peaks of the envelope.

11. A method of estimating a one repetition maximum (1RM), the method comprising:
 receiving a potential signal of a muscle from an electromyography (EMG) sensor attached to a user; and
 estimating a 1RM of the user based on the potential signal.

12. The method of claim 11, wherein the estimating comprises:
 determining an envelope of amplitudes of the potential signal;
 determining a mean frequency of a frequency spectrum of the potential signal; and
 determining a gradient based on the envelope and the mean frequency of the frequency spectrum.

13. The method of claim 12, wherein the determining of the envelope comprises determining the envelope based on an absolute value of the potential signal.

14. The method of claim 12, wherein the determining of the mean frequency of the frequency spectrum comprises determining the mean frequency of the frequency spectrum based on the potential signal sampled at predetermined intervals based on a maximum value of the envelope.

15. The method of claim 12, wherein the determining of the gradient comprises determining the gradient based on a plurality of feature points in the mean frequency of the frequency spectrum corresponding to peaks of the envelope.

* * * * *